(12) United States Patent
Krummradt et al.

(10) Patent No.: US 6,596,865 B1
(45) Date of Patent: Jul. 22, 2003

(54) METHOD OF PURIFYING THIAMINE PHOSPHATES

(75) Inventors: Holger Krummradt, Pfungstadt (DE); Klaus Beschmann, Reinheim (DE); Frank-Hardi Wartenberg, Darmstadt (DE); Horst Diekmann, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/857,792

(22) PCT Filed: Nov. 17, 1999

(86) PCT No.: PCT/EP99/08822
§ 371 (c)(1),
(2), (4) Date: Jun. 11, 2001

(87) PCT Pub. No.: WO00/35927
PCT Pub. Date: Jun. 22, 2000

(30) Foreign Application Priority Data

Dec. 17, 1998 (DE) .......................... 198 58 269

(51) Int. Cl.$^7$ .............................................. C07F 9/6558
(52) U.S. Cl. ...................................................... 544/243
(58) Field of Search ......................................... 544/243

(56) References Cited

U.S. PATENT DOCUMENTS 5,047,223 A * 9/1991 Schul et al. ................ 423/321
5,100,786 A * 3/1992 Shiomi et al. .............. 435/106

FOREIGN PATENT DOCUMENTS

| DE | 1085527 B | 7/1960 |
| DE | 2056076 | 5/1971 |
| EP | 385379 | 9/1990 |
| GB | 793753 A | 4/1958 |
| JP | 50064485 | 5/1975 |

OTHER PUBLICATIONS

Chemical Abstracts vol. 083, No. 13, abstract No. 112410 (MUSHIKA), & JP 50 064485, 1975.

* cited by examiner

Primary Examiner—Deepak Rao
(74) Attorney, Agent, or Firm—Millen, White, Zelano & Branigan, P.C.

(57) ABSTRACT

The invention relates to a method for removing phosphoric acid, thiamine triphosphate and higher thiamine phosphates from solutions that contain phosphoric acid, thiamine monophosphate, thiamine diphosphate, diamine triphosphate and higher phosphates. The inventive method is characterized by passing the phosphoric acid solution of thiamine phosphates over a non-ionogenic adsorber resin which comprises unsaturated cyclic nitrogen bases and eluting thiamine monophosphate and thiamine diphosphate with a suitable solvent.

9 Claims, No Drawings

METHOD OF PURIFYING THIAMINE PHOSPHATES

The invention relates to a process for the separation of phosphoric acid, thiamine triphosphate and higher thiamine phosphates from solutions which contain phosphoric acid and thiamine monophosphate, diphosphate, triphosphate and higher phosphates, characterized in that the phosphoric acid solution of thiamine phosphates is passed over a nonionic adsorber resin which contains unsaturated cyclic nitrogen bases, and thiamine monophosphate and diphosphate are eluted using a suitable solvent.

Thiamine diphosphate (cocarboxylase) is a coenzyme in a number of reactions in which carbon-carbon bonds are cleaved, e.g. in the oxidative decarboxylation of pyruvate to acetyl-CoA and of 2-oxoglutarate to succinyl-CoA, in carbohydrate metabolism and in fermentation processes.

Thiamine diphosphate is employed for the treatment of diabetes, in liver diseases, cardiac insufficiency, convulsions, multiple sclerosis, acidoses etc.

Production on an industrial scale makes the most economical and environmentally compatible preparation necessary.

Customarily, thiamine diphosphate is obtained by phosphorylation of thiamine. In this connection, as a rule a product mixture is obtained which, depending on the reaction conditions, is composed of different proportions of thiamine monophosphate, diphosphate and triphosphate, higher thiamine phosphates and phosphoric acid.

In many cases, the separation of the product mixture is carried out by use of ion exchangers which have a varyingly high affinity for the individual components of the mixture.

Thus DE-A-1 085 527, for example describes that mixtures which contain thiamine monophosphate, diphosphate and triphosphate, higher thiamine phosphates and phosphoric acid can be separated by passing the mixture firstly over a weakly basic ion exchanger, whereby phosphoric acid is removed. The mixture is then led, after a hydrolysis, which is not described in greater detail, of the thiamine triphosphate contained in the mixture, over a cation exchanger, thiamine monophosphate remaining adhered, while thiamine diphosphate is eluted.

It is disadvantageous in this process that the thiamine triphosphate and in general also the higher thiamine phosphates as a rule have to be removed, by hydrolysis or similar measures, from the mixture to be separated before the separation of the thiamine monophosphate from the thiamine diphosphate can take place on the cation exchanger. This means a further process step and is uneconomical for an industrial process.

A similar process is described in GB 793 753, which likewise employs ion exchangers for the separation of the phosphorylation products. In this process, thiamine triphosphate is separated by fractional elution. Since the thiamine tri- and tetraphosphates as a rule have a very similar affinity for the ion exchangers to that of thiamine diphosphate, the elution of the diphosphate overlaps clearly with that of the higher phosphates. The separation of higher thiamine phosphates can therefore as a rule only be achieved with yield restrictions of thiamine diphosphate due to correspondingly large-scale fractionation of the eluate.

A process described in EP 0 385 379 B1, with the aid of which thiamine monophosphate can be separated from mixtures which contains thiamine monophosphate, diphosphate and triphosphate, higher thiamine phosphates and phosphoric acid, likewise proposes employing an ion exchanger and eluting thiamine diphosphate and higher thiamine phosphates using water, while thiamine monophosphate remains on the ion exchanger. In order to obtain the valuable product thiamine diphosphate, the need exists, however, as in the processes mentioned beforehand, to free the thiamine diphosphate from the higher thiamine phosphates according to known methods, which as a rule can be achieved only by yield restrictions of thiamine diphosphate.

It has now been found that phosphoric acid, thiamine triphosphate and higher thiamine phosphates can be separated from solutions which contain phosphoric acid and thiamine monophosphate, diphosphate, triphosphate and higher phosphates if the phosphoric acid solution of thiamine phosphates is passed over a nonionic adsorber resin which contains unsaturated cyclic nitrogen bases, and thiamine monophosphate and diphosphate are eluted using a suitable solvent.

Surprisingly, owing to the use of adsorber resins which contain unsaturated cyclic nitrogen bases, phosphoric acid, thiamine triphosphate and higher thiamine phosphates, essentially tetraphosphate, remain on the adsorber resin and/or are cleaved to thiamine diphosphate, while thiamine monophosphate and thiamine diphosphate are eluted. After removal of the solvent, thiamine monophosphate and diphosphate are obtained in high purity in this way with only very low substance losses.

If an adequate separation of thiamine mono- and diphosphate cannot be achieved by fractional elution, the mixtures of thiamine diphosphate and thiamine monophosphate obtained in this way can be separated by known methods, which are described, for example, in DE-A-1 085 527, GB 793 753 or EP 0 385 379 B1.

Preferably, the mixtures of thiamine diphosphate and thiamine monophosphate are separated by allowing their solutions to run over cation exchangers such as Amberlite IRC 50, IR 100, IR 105 or IR 120 or over cation exchangers which contain aminoethylene and/or iminodimethylenephosphonic acid radicals, such as, for example, Lewatit OC 1060 from Bayer, as such ion exchangers retain thiamine monophosphate and allow the thiamine diphosphate to run through, such that essentially thiamine monophosphate-free solutions of thiamine diphosphate are obtained.

The nonionic adsorber resins are synthetic porous bead polymers which are insoluble in water and organic solvents, where the functional groups, depending on the type and structure of the polymer, can have a more or less polar character. These resins are able to adsorb both anions, cations and uncharged compounds.

Those adsorber resins are preferred which in the polymer-bound form contain the parent structures of the following heterocyclic bases as functional groups: pyrrole, indole, pyridine, quinoline, isoquinoline, acridine, pyridazine, pyrimidine, pyrazine, quinoxaline, pteridine, purine, pyrazole, imidazole, thiazole or oxazole. Preferably, those adsorber resins are used for the process according to the invention which essentially consist of, for example, poly(vinylpyrrole), poly(vinylindole), poly(vinylpyridine), poly(vinylquinoline), poly(vinylisoquinoline), poly(vinylacridine), poly(vinylpyridazine), poly(vinylpyridazine), poly(vinylpyrimidine), poly(vinylpyrazine), poly(vinylquinoxaline), poly(vinylpteridine), poly(vinylpurine), poly(vinylpyrazole), poly(vinylimidazole), poly(vinylthiazole) or poly(vinyloxazole) crosslinked by divinylbenzene or methylenebisacrylamide. Mixtures of various adsorber resins are also suitable.

The invention thus relates to a process for the separation of phosphoric acid, thiamine triphosphate and higher thiamine phosphates from solutions which contain phosphoric acid and thiamine monophosphate, diphosphate, triphosphate and higher phosphates, characterized in that the phosphoric acid solution of thiamine phosphates is passed over a nonionic adsorber resin which contains unsaturated cyclic nitrogen bases, and thiamine monophosphate and diphosphate are eluted using a suitable solvent.

The invention preferably relates to a process for the separation of phosphoric acid, thiamine triphosphate and higher thiamine phosphates from solutions which contain phosphoric acid and thiamine monophosphate, diphosphate, triphosphate and higher phosphates, characterized in that the solution of thiamine phosphates is passed over a nonionic adsorber resin whose polymeric structure is made up of base units which contain at least one of the groups of the formula I or II:

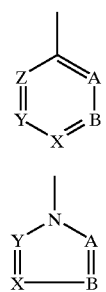

in which one or two of the groups A, B, X, Y and/or Z has/have the meaning N, while the remaining groups are CR, and R independently of one another is H, halogen, alkyl or alkoxy having 1 to 7 C atoms, and thiamine monophosphate and diphosphate are eluted using a suitable solvent.

Preferably, only one of the radicals A, B, X, Y or Z has the meaning N.

In the preferred compounds of the groups of the formula I or II above and below, R is H or an alkyl group having 1 to 3C atoms. R particularly preferably has the meaning H.

Particularly preferred alkyl groups are n-hexyl, n-pentyl, n-butyl, i-butyl, n-propyl, i-propyl, methyl and ethyl, in particular methyl and ethyl. Particularly preferred alkoxy groups are n-hexyloxy, n-pentyloxy, n-butyloxy, i-butyloxy, propyloxy, i-propyloxy, methoxy and ethoxy, in particular methoxy and ethoxy.

Compounds of the above and below formulae having branched groups R can be important. Branched groups of this type as a rule contain not more than two chain branchings. R is preferably a straight-chain group or a branched group having not more than one chain branching.

Halogen is F, Cl, Br or I, in particular F or Cl.

The preferred adsorber resins which are used for the process according to the invention have groups of the formula I or II in which the groups A, B, X, Y and/or Z have at least one of the preferred meanings.

Particularly preferably, nonionic adsorber resins used for the process according to the invention are those whose polymer structure is built up of base units which contain at least one of the groups of the formula I1, I2, I3, I4, II1 or II2:

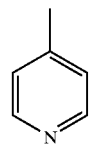

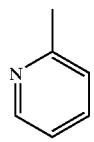

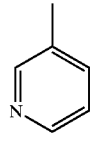

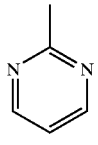

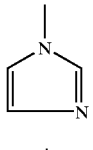

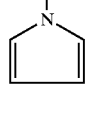

Very particularly preferably, adsorber resins used for the process according to the invention are those whose polymeric structure is made up of base units which contain at least one of the groups of the formula I1 or II1.

Appropriate adsorber resins which contain unsaturated cyclic nitrogen bases as functional groups are known and commercially obtainable (e.g. from Riedel-de-Haen, Seelze, Germany or Reilly Industries Inc. Indianapolis) or can be prepared analogously to known processes (e.g. Pure Appl. Chem. 1967, 15(3–4), 453–464, J. Polym. Sci., Polym. Lett. Ed. 1966, 4(11), 797–801 or DE 20 56 076).

Particularly preferably, suitable adsorber resins are those supplied by Riedel-de-Haen under the name adsorber resin VP-8, VI-9 or VI-15 or those from Reilly under the name Reillex 402, Reillex 425, Reillex HP or Reillex HPQ, which contain pyridyl groups of the formula I1 or imidazoyl groups of the formula II1.

The process according to the invention which is particularly preferred is the one which is characterized in that the solution of thiamine phosphates is passed over one or more of the following adsorber resins: adsorber resin VP-8, VI-9 or VI-15 from Riedel-de-Haen or Reillex 402, Reillex 425, Reillex HP or Reillex HPQ from Reilly Industries.

These adsorber resins essentially consist of crosslinked poly(4-vinylpyridine) or poly(n-vinylimidazole), which, depending on the degree of crosslinking, has been polymerized with different proportions of methylenebisacrylamide or divinylbenzene.

Adsorber resins which essentially consist of crosslinked poly(4-vinylpyridine) are preferably employed for the process according to the invention.

The adsorber resins mentioned are distinguished by a particularly high selectivity and surprisingly high capacity for the binding of phosphoric acid. The phosphoric acid esters of thiamine are obtained, for example, according to DE 663 588, DE 704 172, DE 706 835, DE 708 514, DE 729 905, US 2 188 323 or US 2 435 750. Generally, however, use can also be made of variants which are known per se, but not mentioned here in greater detail, in order to prepare the thiamine phosphates.

The process according to the invention is simple to carry out, the solution of thiamine phosphates, preferably a solution of thiamine phosphates such as is formed, for example, in the phosphorylation of thiamine with concentrated phosphoric acid, optionally being freed from an excess of phosphoric acid as described in DE 1085 527 and this solution being passed, preferably between 5° C. and 50° C., in particular preferably at room temperature, over an adsorber resin which contains unsaturated cyclic nitrogen bases and is situated in a customary chromatography column. The column volume in this case approximately corresponds to that of the resin volume.

Elution is preferably carried out using a flow rate of ⅕ of the column volume per hour up to ¾ of the column volume per hour, preferably using ¼ of the column volume per hour up to half of the column volume per hour.

By means of elution with a suitable solvent, a solution of the thiamine monophosphate and diphosphate is obtained. It is likewise possible to achieve a separation of the monophosphate from the diphosphate by fractional elution.

Preferably, however, thiamine monophosphate and thiamine diphosphate are eluted together and a separation of these thiamine phosphates is brought about according to the known methods.

The elution is preferably monitored by pH checking of the eluate. Depending on the adsorber resin used, the elution of the thiamine monophosphate and thiamine diphosphate is carried out as a rule at pH values of the eluate of between pH 10 and pH 2, preferably between pH 9 and pH 3. By collection of the eluate which has a pH between the values mentioned and removal of the solvent, the mixtures of the thiamine monophosphate and thiamine diphosphate can be obtained as a solid.

The solvent used for elution is preferably water. However, it is also possible to employ water-miscible organic solvents. These are, for example, alcohols such as methanol, ethanol or isopropanol, ketones such as acetone or methyl ethyl ketone, carboxylic acids such as formic acid or acetic acid, organic nitrites such as acetonitrile, ethers such as tetrahydrofuran or dioxane, sulfoxides such as dimethyl sulfoxide or amides such as N-methylpyrrolidone or N,N-dimethylformamide. Mixtures of the solvents mentioned can also be used, in particular aqueous solutions of the organic solvents mentioned.

If water or aqueous solutions of organic solvents are employed as eluent, inorganic acids such as hydrochloric acid or sulfuric acid can be added to the eluent.

For the regeneration of the adsorber resin after the elution of thiamine monophosphate and diphosphate, the resin is preferably rinsed with a base in order to wash out the phosphoric acid and the thiamine monophosphate bound in the resin. Bases used are preferably solutions of alkali metal hydroxides and carbonates or nitrogen bases. In particular, aqueous solutions of potassium hydroxide or sodium hydroxide or carbonate or aqueous ammonia solution are employed. Very particularly preferably, aqueous ammonia solution is suitable as a base for the regeneration of the adsorber resin. The ammonia solution is preferably 0.5 to 20%, in particular 1 to 10%.

Before and after the treatment of the adsorber resin with a suitable base, the resin is preferably rinsed with water. In this way, some of the phosphoric acid adhering to the resin is removed before the use of the base. By rinsing after use of the base, a possible excess of the base is removed.

If aqueous ammonia solution is used as base, it has proved expedient to recover the ammonium phosphate formed in the regeneration of the adsorber resin as a by-product after removal of the solvent.

By means of the process according to the invention, it is possible in a single process step to obtain mixtures of the valuable products thiamine monophosphate and thiamine diphosphate with only very low substance losses and in high purity from mixtures which are obtained by phosphorylation of thiamine.

Even without further embodiments, it is assumed that a person skilled in the art can utilize the above description to the widest extent. The preferred embodiments are therefore only to be interpreted as descriptive, and in no way as limiting disclosure in any manner.

The following example is intended to illustrate the invention without restricting it. Above and below, percentages mean percentage by weight. All temperatures are indicated in degrees Celsius.

EXAMPLE 2 kg of thiaminium dichloride are phosphorylated in a customary manner and the reaction mixture obtained is passed over a loose layer of 40 l of adsorber resin Reillex HP. Elution is then carried out using water, and the fraction collected between pH 9 and 3 is freed from the solvent. The mixture of thiamine monophosphate and thiamine diphosphate obtained in this manner is essentially free of phosphoric acid, thiamine triphosphate and higher thiamine phosphates.

For the regeneration of the adsorber resin, the resin is first rinsed with water and then with aqueous ammonia solution until the solution flowing out has reached a pH of approximately 12. After rinsing with water again, as soon as the solution flowing out has reached a pH of 9 to 7 the resin is again ready for use.

What is claimed is:

1. A process for the separation of phosphoric acid, thiamine triphosphate and higher thiamine phosphates from solutions which contain phosphoric acid and thiamine monophosphate, diphosphate, triphosphate and higher phosphates, comprising passing a phosphoric acid solution of thiamine phosphates over a nonionic adsorber resin which contains at least one unsaturated cyclic nitrogen base, and eluting thiamine monophosphate and diphosphate with a solvent.

2. A process as claimed in claim 1, wherein the solution of thiamine phosphates is passed over a nonionic adsorber resin whose polymeric structure is built up of base units which contain at least one of the groups of formula I or II:

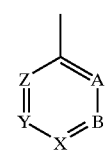

I

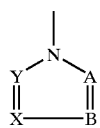

II in which one or two of the groups A, B, X, Y and/or Z are N, the remaining groups are CR and each R independently is H, halogen, or alkoxy having 1 to 7 C atoms.

3. A process as claimed in claim 1, wherein the solution of thiamine phosphates is passed over a nonionic adsorber resin whose polymeric structure is built up of base units which contain at least one group of formula I1, I2, I3, I4, II1 or II2:

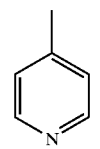

I1

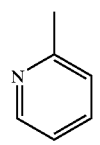

I2

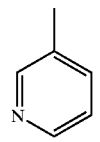

I3

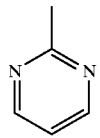

I4

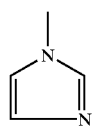

II1

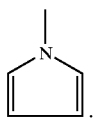

II2

4. A process as claimed in claim 1, wherein the solution of thiamine phosphates is passed over an adsorber resin at temperatures between 5° C. and 50° C. and eluted using water.

5. A process as claimed in claim 1, further comprising recovering essentially thiamine monophosphate-free solution of thiamine diphosphate.

6. A process according to claim 1, further comprising separating thiamine monophosplate from thiamine diphosphate by fractional elution.

7. A process according to claim 1, further comprising separating thiamine monophosphate from thiamine diphosphate by contacting a mixture of thiamine mono- and diphosphate with a cation exchanger.

8. A process for the separation of phosphoric acid, thiamine triphosphate and higher thiamine phosphates from solutions which contain phosphoric acid and thiamine monophosphate, diphosphate, triphosphate and higher phosphates, comprising passing a phosphoric acid solution of thiamine phosphates over a nonionic adsorber resin which contains at least one unsaturated cyclic nitrogen base.

9. A process for the separation of phosphoric acid, thiamine triphosphate and higher thiamine phosphates from solutions which contain phosphoric acid and thiamine monophosphate, diphosphate, triphosphate and higher phosphates, comprising phosphorylating thiamine, and passing a phosphoric acid solution of thiamine phosphates over a nonionic adsorber resin which contains at least one unsaturated cyclic nitrogen base.

* * * * *

UNITED STATES PATENT AND TRADEMARK OFFICE
CERTIFICATE OF CORRECTION

PATENT NO. : 6,596,865 B1
DATED : July 22, 2003
INVENTOR(S) : Holger Krummradt et al.

It is certified that error appears in the above-identified patent and that said Letters Patent is hereby corrected as shown below:

Column 7,
Line 12, reads "halogen, or alkoxy" should read -- halogen, alkyl or alkoxy --

Signed and Sealed this

Seventeenth Day of August, 2004

JON W. DUDAS
*Acting Director of the United States Patent and Trademark Office*